United States Patent
Destarac

(10) Patent No.: US 7,737,237 B2
(45) Date of Patent: Jun. 15, 2010

(54) CONTROLLED STRUCTURE COPOLYMER COMPRISING AN AMPHOTERIC OR ZWITTERIONIC PART

(75) Inventor: Mathias Destarac, Paris (FR)

(73) Assignee: Phodia Chimie, Aubervilliers (FR)

( * ) Notice: Subject to any disclaimer, the term of this patent is extended or adjusted under 35 U.S.C. 154(b) by 1018 days.

(21) Appl. No.: 10/534,196

(22) PCT Filed: Oct. 31, 2003

(86) PCT No.: PCT/FR03/03255

§ 371 (c)(1),
(2), (4) Date: Apr. 3, 2006

(87) PCT Pub. No.: WO2004/044023

PCT Pub. Date: May 27, 2004

(65) Prior Publication Data

US 2006/0217285 A1    Sep. 28, 2006

(30) Foreign Application Priority Data

Nov. 7, 2002 (FR) .................. 02 13950
Aug. 29, 2003 (FR) .................. 03 10292

(51) Int. Cl.
*C08F 220/60* (2006.01)
*C08F 20/06* (2006.01)

(52) U.S. Cl. .............. 526/307.4; 526/271; 526/277; 526/287; 526/288; 526/303.1; 526/307; 526/307.6; 526/307.7; 526/310; 526/318.4; 526/328.5; 526/329.2; 526/329.3; 526/342; 526/343; 526/344; 526/347; 526/347.1; 526/348

(58) Field of Classification Search ............ 526/271, 526/277, 287, 288, 303.1, 307, 307.6, 307.7, 526/310, 318.4, 328.5, 329.2, 329.3, 342, 526/343, 344, 347, 347.1
See application file for complete search history.

(56) References Cited

U.S. PATENT DOCUMENTS

| | | | | |
|---|---|---|---|---|
| 4,395,444 A | * | 7/1983 | Das et al. ................. | 427/388.4 |
| 6,174,963 B1 | * | 1/2001 | Tamazawa et al. ......... | 525/193 |
| 7,071,156 B2 | * | 7/2006 | Aubay et al. ............... | 510/475 |
| 7,141,519 B2 | * | 11/2006 | Bunyard et al. ............ | 442/327 |

FOREIGN PATENT DOCUMENTS

| | | | |
|---|---|---|---|
| JP | 09-279084 | * | 10/1997 |
| WO | WO02/28929 | * | 4/2002 |

\* cited by examiner

*Primary Examiner*—Helen L. Pezzuto
(74) *Attorney, Agent, or Firm*—Hunton & Williams LLP

(57) ABSTRACT

The present invention concerns a controlled structure copolymer comprising at least two different parts, a first part A, amphoteric or zwitterionic, including anionic or potentially anionic units, and cationic or potentially cationic units, or zwitterionic units, and another part B, non amphoteric or zwitterionic. Said copolymer further exhibits a high potential for adaptation, through variation in its composition, in order to improve or modify the properties of compositions in which it is introduced.

14 Claims, No Drawings

CONTROLLED STRUCTURE COPOLYMER COMPRISING AN AMPHOTERIC OR ZWITTERIONIC PART

This application is an application under 35 U.S.C. Section 371 of International Application Number PCT/FR2003/003255 filed on Oct. 31, 2003.

The present invention relates to a novel family of polymers. Many polymer structures and many compositions are known. There are, for example, homopolymers, linear random copolymers or linear sequenced copolymers (block copolymers), comb or grafted polymers or copolymers, and star polymers or copolymers. The composition of a copolymer is related to the various units included in the polymeric chains. The various units can derive from various monomers and/or can result from a chemical reaction carried out after the polymerization process. Among copolymers, random copolymers comprising neutral hydrophobic units, anionic or potentially anionic units, and cationic or potentially cationic units are known. It is specified that random copolymer are generally obtained by introducing various monomers together into a polymerization reaction medium. Such copolymers are non-controlled structure polymers. These polymers have advantageous properties, which can make them useful in compositions such as detergent compositions, for playing the role of a deposit on surfaces, or for initiating a process of precipitation of other compounds by a variation in outside conditions such as the pH.

Recently, methods for preparing controlled structure polymers have been developed, in particular for obtaining block copolymers. Thus, it has been found that methods and operating conditions exist for preparing block copolymers having two blocks, of the type (hydrophilic neutral)-block-(hydrophilic anionic), (hydrophilic neutral)-block-(hydrophilic cationic), (hydrophobic neutral)-block-(hydrophilic neutral), (hydrophobic neutral)-block-(hydrophilic anionic), or (hydrophobic neutral)-block-(hydrophilic cationic). These various polymer families are found to be useful in certain compositions.

However, new polymers for obtaining novel compositions or novel physicochemical systems are still being sought.

Thus, the invention proposes a controlled structure copolymer comprising at least two different parts, a first part A, amphoteric or zwitterionic, comprising anionic or potentially anionic units, and cationic or potentially cationic units, or zwitterionic units, and another part B, non amphoteric or zwitterionic. It also exhibits a high potential for adaptation, through variation of its composition, in order to improve or modify the properties of compositions into which it is introduced, or more simply in order to propose novel compositions or physicochemical systems. In other words, the invention proposes a novel copolymer exhibiting great modularity. It is thus possible to modulate the properties of an amphoteric or zwitterionic, random copolymer by adding a block, for example a neutral block, or to couple the properties of several sequences, including an amphoteric sequence.

The copolymer according to the invention finds uses in many fields, in particular in the fields of detergence, of fabric care, of cosmetics, and of compositions intended to cleanse, treat or protect the skin or the hair. The invention therefore also concerns the use of the copolymer in detergent compositions, fabric care compositions, or compositions for cleansing, treating and/or protecting the skin and/or the hair.

The controlled structure copolymer comprises at least two parts A and B of different compositions, part A comprising ionic or potentially ionic units, characterized in that:

part A is an amphoteric or zwitterionic part, comprising:
    cationic or potentially cationic units $A_C$,
    anionic or potentially anionic units $A_A$, and
    optionally, hydrophilic and/or hydrophobic neutral units $A_N$,
and/or
    zwitterionic units $A_Z$,
    optionally, cationic or potentially cationic units $A_C$,
    optionally, anionic or potentially anionic units $A_A$, and
    optionally, hydrophilic and/or hydrophobic neutral units $A_N$,
part B is not an amphoteric or zwitterionic part.

The parts of a controlled structure copolymer can in particular be blocks, linear backbones, side chains, grafts, "hairs" or branches of microgels or of stars, cores of stars or of microgels, or alternatively parts of polymeric chains having various concentrations of various units.

Thus, the controlled structure that the copolymer according to the invention exhibits can be chosen from the following structures:

block copolymer, comprising at least two blocks, part A corresponding to one block, part B corresponding to another. Part A most commonly consists of several different units, having, where appropriate, a composition gradient. Part A can also have a random copolymer structure. Thus, part A can have a homopolymer (if it comprises $A_Z$ units), random copolymer or composition-gradient copolymer structure;

comb or grafted copolymer, comprising a backbone and side chains, with part A corresponding to the backbone and part B corresponding to side chains, or with part B corresponding to the backbone and part A corresponding to side chains;

star or microgel copolymer, comprising a polymeric or nonpolymeric core, and peripheral polymeric chains, one part corresponding to the core, the other corresponding to the peripheral chains. Part A can correspond to the core and part B can correspond to the peripheral chains. Conversely, part B can correspond to the core and part A can correspond to the peripheral chains.

According to a particularly advantageous embodiment, the copolymer is a block copolymer, for example a (block A)-(block B) diblock copolymer, a (block A)-(block B)-(block A) triblock copolymer or a (block B)-(block A)-(block B) triblock copolymer.

Definitions

In the present application, the expression "unit derived from a monomer" denotes a unit that can be obtained directly from said monomer by polymerization. Thus, for example, a unit derived from an acrylic or methacrylic acid ester does not cover a unit of formula —$CH_2$—$CH(COOH)$—, —$CH_2$—$C(CH_3)(COOH)$—, —$CH_2$—$CH(OH)$—, respectively, obtained for example by polymerizing an acrylic or methacrylic acid ester, or vinyl acetate, respectively, and then hydrolyzing. A unit derived from acrylic or methacrylic acid covers, for example, a unit obtained by polymerizing a monomer (for example an acrylic or methacrylic acid ester), and then reacting (for example by hydrolysis) the polymer obtained so as to obtain units of formula —$CH_2$—$CH(COOH)$—, or —$CH_2$—$C(CH_3)(COOH)$—. A unit derived from a vinyl alcohol covers, for example, a unit obtained by polymerizing a monomer (for example a vinyl ester), and then by reacting (for example by hydrolysis) the polymer obtained so as to obtain units of formula —$CH_2$—$CH(OH)$—.

In the present application, unless otherwise mentioned, the average molar masses are number-average molar masses, measured by stearic exclusion chromatography in an appropriate solvent, coupled to a multiangle light scattering detector (GPC-MALLS). In the present application, reference may also be made to theoretical average molar masses, determined from the masses of constituents used to prepare the polymers.

Typically, the theoretical average molar mass M of a block, of a side chain, of a backbone, of peripheral chains or of a core is calculated according to the following formula:

$$M = \sum_i M_i * \frac{n_i}{n_{precursor}}$$

where $M_i$ is the molar mass of a monomer i, $n_i$ is the number of moles of the monomer i, $n_{precursor}$ is the number of moles of a compound to which the macromolecular chain of the block, side chain, backbone, peripheral chain or core will be attached. This compound may be a transfer agent (or a transfer group) or an initiator, a preceding block, etc. If it is a preceding block, the number of moles can be considered to be the number of moles of a compound to which the macromolecular chain of said preceding block was attached, for example a transfer agent (or a transfer group) or an initiator.

In the present invention, the expression "an average charge Q of a part" denotes the charge defined by the following equation:

$$Q = \frac{[c]X_c - [a]X_a}{[c]X_c + [a]X_a}$$

where:

[c] is the molar concentration of units $A_C$ in part A,

[a] is the molar concentration of units $A_A$ in part A, $X_C$ represents the degree of possible neutralization of the units $A_C$ (in the case where the units $A_C$ are potentially cationic); $X_C=[BH^+]/([B]+[BH^+])$, $X_A$ represents the degree of possible neutralization of the units $A_A$ (in the case where the units $A_C$ are potentially anionic); $X_A=[A^-]/([AH]+[A^-])$.

In the present application, the term "hydrophobic" is used in its usual sense of "that which has no affinity for water"; this means that the organic polymer of which it consists, taken alone, (of the same composition and of the same molar mass), would form a two-phase macroscopic solution in distilled water at 25° C., at a concentration of greater than 1% by weight.

In the present application, the term "hydrophilic" is also used in its usual sense of "that which has affinity for water", i.e. that which is not capable of forming a two-phase macroscopic solution in distilled water at 25° C. at a concentration of greater than 1% by weight.

According to a particularly advantageous embodiment, the weight ratio of part B to part A is from 0.01 to 100, for example from 0.01 to 1, preferably from 0.1 to 1 or from 1 to 100, preferably from 1 to 10. It is a weight ratio between the amount of monomers used to obtain the copolymer. This ratio is also the ratio of the theoretical average molar masses.

According to an advantageous embodiment, the copolymer is water-soluble soluble or water-dispersible. This means that said copolymer does not, over at least a certain pH and concentration range, form a two-phase composition in water, under the conditions of use.

Preferably, parts A and B derive from ethylenically unsaturated monomers.

The copolymer according to the invention may in particular be in the form of a powder, in the form of a dispersion in a liquid, or in the form of a solution in a solvent (water or other). The form generally depends on the requirements associated with the use of the copolymer. It may also be associated with the method of preparing the copolymer.

Preferably, the units of parts A and B derive from ethylenically unsaturated monomers, more preferably α,β-monoethylenically unsaturated monomers.

Part B

Part B (for example, block B) is a polymeric part that does not correspond to an amphoteric or zwitterionic part. In other words, part B does not comprise units derived from zwitterionic monomers, or does not simultaneously comprise cationic or potentially cationic units and anionic or potentially anionic units. Part B is preferably a hydrophilic or hydrophobic neutral part comprising units derived from hydrophilic or hydrophobic neutral monomers. The copolymers in which part B is a hydrophobic neutral part are particularly advantageous. Preferably, part B is essentially nonionic or nonionizable at the pH at which the copolymer is used. Most preferably, part B is nonionic. For example, part B (for example, block B) derives from at least one hydrophobic nonionic monomer.

Part B can also contain hydrophilic nonionic units derived from at least one hydrophilic nonionic monomer, in an amount sufficiently small for the block to conserve a hydrophobic nature; this amount can range up to 10 mol % of all the monomers from which said part B (for example, block B) derives.

Similarly, part B can also contain ionic or potentially ionic (in particular cationic or potentially cationic) units derived from at least one ionic or potentially ionic (in particular cationic or potentially cationic) monomer, in a minimal amount, so that said polymer conserves its hydrophobic and essentially nonionic nature; this amount can range up to 10 mol % of all the monomers from which said part B (for example, block B) derives.

By way of examples of hydrophobic nonionic monomers from which part B (for example, block B) can derive, mention may be made of:

vinylaromatic monomers such as styrene, alpha-methylstyrene, vinyltoluene, etc., vinyl halides or vinylidene halides, such as vinyl chloride, vinylidene chloride, $C_1$-$C_{12}$ alkylesters of α,β-monoethylenically unsaturated acids such as methyl, ethyl or butyl acrylates and methacrylates, 2-ethylhexyl acrylate, etc., vinyl esters or allyl esters of saturated carboxylic acids, such as vinyl or allyl acetates, propionates, versatates, stearates, etc., α,β-monoethylenically unsaturated nitriles containing from 3 to 12 carbon atoms, such as acrylonitrile, methacrylonitrile, etc., α-olefins such as ethylene, etc., conjugated dienes, such as butadiene, isoprene, chloroprene, monomers capable of generating polydimethylsiloxane (PDMS) chains.

Thus, part B can be a silicone, for example a polydimethylsiloxane chain or a copolymer comprising dimethylsiloxy units.

By way of examples of possible nonionic hydrophilic monomers, mention may be made of:

hydroxyalkyl esters of α,β-ethylenically unsaturated acids, such as hydroxyethyl or hydroxypropyl acrylates and methacrylates, glyceryl monomethacrylate, etc., α,β-ethylenically unsaturated amides such as acrylamide, N,N-dimethylmethacrylamide, N-methylolacrylamide, etc., α,β-ethylenically unsaturated monomers bearing a water-soluble polyoxyalkylene segment of the poly(ethylene oxide) type, such as poly(ethylene oxide) α-methacrylates (Bisomer S20W, S10W, etc., from Laporte) or α,ω-dimethacrylates, Sipomer BEM from Rhodia (ω-behenyl polyoxyethylene methacrylate), Sipomer SEM-25 from Rhodia (ω-tristyrylphenyl polyoxyethylene methacrylate), etc., α,β-ethylenically unsaturated monomers which are precursors of hydrophilic units or segments, such as vinyl acetate, which, once polymerized, can be hydrolyzed in order to give rise to vinyl alcohol units or polyvinyl alcohol segments, vinylpyrrolidones, α,β-ethylenically unsaturated monomers of the ureido type, and in particular 2-imidazolidinone-ethyl methacrylamide (Sipomer WAM II from Rhodia).

Examples of ionic or potentially ionic monomers that can be used in a minor amount are mentioned below (with regard to part A).

The average molecular mass of part B (for example, block B) can range from 500 to 100 000, preferably from 500 to 25 000 g/mol, measured by stearic exclusion chromatography.

Part A

Part A comprises ionic or potentially ionic units. It is an amphoteric or zwitterionic part comprising:

in the case of an amphoteric part:
cationic or potentially cationic units $A_C$,
anionic or potentially anionic units $A_A$, and
optionally, hydrophilic and/or hydrophobic neutral units $A_N$, and/or in the case of a zwitterionic part:
zwitterionic units $A_Z$,
optionally, cationic or potentially cationic units $A_C$,
optionally, anionic or potentially anionic units $A_A$, and
optionally, hydrophilic and/or hydrophobic neutral units $A_N$.

In part A, the units $A_C$, $A_A$ and, optionally, $A_N$ are preferably in the form of a random or gradient copolymer. It is not, however, impossible for them to be in the form of a slightly blocky copolymer. Part A can consist only of units AZ, but generally, the zwitterionic part is a random copolymer, or gradient copolymer, comprising, in addition to the units AZ, units chosen from the units $A_C$, $A_A$ and/or $A_N$.

The expression "cationic or potentially cationic units $A_C$" is intended to mean units that comprise a cationic or potentially cationic group. The cationic units or groups are units or groups that have at least one positive charge (generally associated with one or more anions such as the chloride ion, the bromide ion, a sulfate group, a methyl sulfate group), whatever the pH of the medium in which the copolymer is present. The potentially cationic units or groups are units or groups that may be neutral or may have at least one positive charge according to the pH of the medium in which the copolymer is present. In this case, reference will be made to potentially cationic units $A_C$ in neutral form or in cationic form. By extension, reference may be made to cationic or potentially cationic monomers.

The expression "anionic or potentially anionic units $A_A$" is intended to mean units that comprise an anionic or potentially anionic group. The anionic units or groups are units or groups that have at least one negative charge (generally associated with one or more cations such as cations of alkali metal or alkaline earth metal, for example sodium, compounds, or cationic groups such as ammonium), whatever the pH of the medium in which the copolymer is present. The potentially anionic units or groups are units or groups that may be neutral or may have at least one negative charge according to the pH of the medium in which the copolymer is present. In this case, reference will be made to potentially anionic units $A_A$ in neutral form or in anionic form. By extension, reference may be made to anionic or potentially anionic monomers.

The term "neutral units $A_N$" is intended to mean units that have no charge, whatever the pH of the medium in which the copolymer is present.

Part A can simultaneously have potentially cationic units $A_C$ in cationic form, and anionic or potentially anionic units $A_A$ in anionic form. Alternatively, part A can simultaneously have cationic or potentially cationic units $A_C$ in cationic form, and potentially anionic units $A_A$ in neutral form. Alternatively, part A can simultaneously have potentially cationic units $A_C$ in neutral form, and anionic or potentially anionic units $A_A$ in anionic form. Preferably, the copolymer does not simultaneously have units $A_A$ and units $A_C$ in neutral form.

The units $A_N$ can be hydrophilic or hydrophobic. Preferably, they are hydrophobic, but can comprise hydrophilic units.

By way of examples of potentially cationic hydrophilic monomers (from which units $A_C$ can derive), mention may be made of:

N,N-(dialkylamino-ω-alkyl)amides of α,β-monoethylenically unsaturated carboxylic acids, such as N,N-dimethylaminomethylacrylamide or -methacrylamide, 2-(N,N-dimethylamino)ethylacrylamide or -methacrylamide, 3-(N,N-dimethylamino)propylacrylamide or -methacrylamide, and 4-(N,N-dimethylamino)butylacrylamide or -methacrylamide, α,β-monoethylenically unsaturated amino esters such as 2-(dimethylamino)ethyl acrylate (DMAA), 2-(dimethylamino)ethyl methacrylate (DMAM), 3-(dimethylamino)propyl methacrylate, 2-(tert-butylamino)ethyl methacrylate, 2-(dipentylamino)ethyl methacrylate, and 2-(diethylamino)ethyl methacrylate, vinylpyridines, vinylamine, vinylimidazolines, monomers that are precursors of amine functions such as N-vinylformamide, N-vinylacetamide, etc., which give rise to primary amine functions by simple acid or base hydrolysis.

By way of examples of cationic hydrophilic monomers, from which units $A_C$ can derive, mention may be made of:

acryloyl- or acryloyloxyammonium monomers such as trimethylammonium propyl methacrylate chloride, trimethylammonium ethylacrylamide or -methacrylamide chloride or bromide, trimethylammonium butylacrylamide or -methacrylamide methyl sulfate, trimethylammonium propylmethacrylamide methyl sulfate (MES), (3-methacrylamidopropyl)trimethylammonium chloride (MAPTAC), (3-acrylamidopropyl)trimethylammonium chloride (APTAC), methacryloyloxyethyltrimethylammonium chloride or methyl sulfate, and acryloyloxyethyltrimethylammonium chloride;

1-ethyl-2-vinylpyridinium or 1-ethyl-4-vinylpyridinium bromide, chloride or methyl sulfate;

N,N-dialkyldiallylamine monomers such as N,N-dimethyldiallylammonium chloride (DADMAC);

polyquaternary monomers such as dimethylaminopropylmethacrylamide chloride and N-(3-chloro-2-hydroxypropyl)trimethylammonium (DIQUAT), etc.

Examples of hydrophilic or hydrophobic nonionic (neutral) monomers, from which units $A_N$ can derive, have already been mentioned above (with regard to part B).

By way of examples of anionic or potentially anionic monomers, from which units $A_A$ can derive, mention may be made of:

monomers having at least one carboxylic function, for instance α,β-ethylenically unsaturated carboxylic acids or the corresponding anhydrides, such as acrylic, methacrylic or maleic acids or anhydrides, fumaric acid, itaconic acid, N-methacroylalanine, N-acryloylglycine, and their water-soluble salts, monomers that are precursors of carboxylate functions, such as tert-butyl acrylate, which, after polymerization, give rise to carboxylic functions by hydrolysis, monomers having at least one sulfate or sulfonate function, such as 2-sulfooxyethyl methacrylate, vinylbenzene sulfonic acid, allyl sulfonic acid, 2-acrylamido-2-methylpropane sulfonic acid, sulfoethyl acrylate or methacrylate, sulfopropyl acrylate or methacrylate, and their water-soluble salts, monomers having at least one phosphonate or phosphate function, such as vinylphosphonic acid, etc., the esters of ethylenically unsaturated phosphates, such as the phosphates derived from hydroxyethyl methacrylate (Empicryl 6835 from Rhodia) and those derived from polyoxyalkylene methacrylates, and their water-soluble salts.

By way of examples of zwitterionic monomers, from which units $A_Z$ can derive, mention may be made of:

sulfobetaine monomers, such as sulfopropyl dimethylammonium ethyl methacrylate (SPE from Raschig), sulfopropyldimethylammonium propylmethacrylamide (SPP from Raschig), and sulfopropyl-2-vinylpyridinium (SPV from Raschig), phosphobetaine monomers, such as phosphatoethyl trimethylammonium ethyl methacrylate, carboxybetaine monomers.

The number-average molar mass of part A can range from 500 to 100 000, preferably from 500 to 25 000 g/mol, measured by stearic exclusion chromatography.

In particular, the number-average molar mass of the copolymer according to the invention is between 1000 and 200 000 g/mol, preferably between 1000 and 50 000 g/mol, more particularly between 3000 and 30 000 g/mol, determined by GPC coupled to the MALLS method (Multi Angle Laser Light Scattering).

Part A has a positive, negative or neutral average charge Q. In the case of a zwitterionic part A, the average charge is generally neutral. In the case of an amphoteric part A, the properties of the polymer, and its uses, can be modulated by varying the average charge. In a particular embodiment, part B is a neutral part, and part B has a positive, negative or neutral average charge Q.

By way of examples of diblock copolymers, mention may in particular be made of (poly(butyl acrylate))-(poly(acrylic acid-stat-quaternized 2-dimethylaminoethyl acrylate)) copolymers. By way of example of triblock polymers, mention may in particular be made of (poly(acrylic acid-stat-quaternized 2-dimethylaminoethyl acrylate))-polyorganosiloxanes-(poly(acrylic acid-stat-quaternized 2-dimethylaminoethyl acrylate))-copolymers.

The copolymers according to the invention can be obtained by any known method, whether by controlled or non-controlled radical polymerization, by ring-opening polymerization (in particular anionic or cationic), by anionic or cationic polymerization, or alternatively by chemical modification of a polymer.

Preferably, "living" or "controlled" radical polymerization methods may be carried out.

By way of example of "living" or "controlled" polymerization processes, reference may in particular be made to:

the processes of applications WO 98/58974, WO 00/75207 and WO 01/42312, which employ a radical polymerization controlled by control agents of xanthate type, the process for radical polymerization controlled by control agents of dithioester type of application WO 98/01478, the process described in application WO 02/08307, in particular for obtaining copolymers comprising polyorganosiloxane blocks, the process for radical polymerization controlled by control agents of dithiocarbamate type of application WO 99/31144, the process for radical polymerization controlled by control agents of dithiocarbazate type of application WO 02/26836, the process for radical polymerization controlled by control agents of dithiophosphoro ester type of application WO 02/10223, (optionally, the block copolymers obtained as above by controlled radical polymerization can undergo a reaction for purification of their sulfur-containing chain end, for example by means of processes of the hydrolysis, oxidation, reduction, pyrolysis or substitution type), the process of application WO 99/03894, which employs a polymerization in the presence of nitroxide precursors, the process of application WO 96/30421, which uses atom transfer radical polymerization (ATRP), the process for radical polymerization controlled by control agents of iniferter type according to the teaching of Otu et al., Makromol. Chem. Rapid. Commun., 3, 127 (1982), the process for radical polymerization controlled by degenerative transfer of iodine according to the teaching of Tatemoto et al., Jap. 50, 127, 991 (1975), Daikin Kogyo Co ltd Japan and Matyjaszewski et al., Macromolecules, 28, 2093 (1995), the process for radical polymerization controlled by tetraphenylethane derivatives, disclosed by D. Braun et al., in Macromol. Symp. 111, 63 (1996), or the process for radical polymerization controlled by organocobalt complexes described by Wayland et al., in J. Am. Chem. Soc. 116, 7973 (1994), the process for radical polymerization controlled by diphenylethylene (WO 00/39169 or WO 00/37507).

When the copolymers involved are copolymers with a controlled, grafted or comb architecture, said copolymers can be obtained by "direct grafting" methods and copolymerization. The direct grafting consists in polymerizing the monomer(s) chosen, by radical polymerization, in the presence of the polymer selected to form the backbone of the final product. If the monomer/backbone couple and also the operating conditions are judiciously selected, then a transfer reaction can take place between the growing macroradical and the backbone. This reaction generates a radical on the backbone and it is from this radical that the graft grows. The primary radical derived from the initiator can also participate in the transfer reactions.

As regards the copolymerization, it initially uses grafting, to the end of the future pendant segment, of a function that can be polymerized by radical polymerization. This grafting can be carried out by conventional organic chemistry methods. Then, in a second step, the macromonomer thus obtained is polymerized with the monomer chosen to form the backbone, and a "comb" polymer is obtained. The grafting can advantageously be carried out in the presence of a polymerization controlling agent as mentioned in the references above.

The processes for preparing star-shaped polymers can essentially be classified in two groups. The first corresponds to the formation of the arms of the polymers from a plurifunctional compound constituting the center ("core-first" technique) (Kennedy, J. P. and coll. *Macromolecules*, 29, 8631 (1996), Deffieux, A. and coll. Ibid, 25, 6744, (1992), Gnanou, Y. and coll. Ibid, 31, 6748 (1998)) and the second corresponds to a method in which the polymer molecules which will constitute the arms are first synthesized and then attached together on a core, so as to form a star-shaped polymer ("arm-first" technique).

By way of example of synthesis of this type of polymer, reference may be made to patent WO 00/02939. Mention may also be made of the processes of polymerization from a core comprising several transfer groups, and the micelle crosslinking processes.

Other details or advantages of the invention will emerge more clearly in view of the following example, which is not limiting in nature.

The abbreviations given have the following meaning:

| | |
|---|---|
| * P(ABu) | Homopolymer of butyl acrylate (ABu) |
| * P(ADAME) | Block homopolymer of dimethylaminoethyl acrylate (ADAME) |
| * P(ADAMQuat) | Block homopolymer of trimethyl-ammonium ethyl acrylate methyl sulfate (ADAMQuat) |
| * P(AAstatADAMQuat) | Random block copolymer of acrylic acid and of ADAMQuat, with an AA/ADAMQuat weight ratio of 30/70 |

Synthesis of a poly(butyl acrylate) poly(acrylic acid-stat-quaternized 2-dimethylaminoethyl acrylate) diblock copolymer 124.2 g of ethanol, 13.54 g of O-ethyl-S-(1-methoxycarbonyl)ethylenyl) xanthate ($CH_3CHCO_2CH_3)S(C=S)OEt$ and 65 g of butyl acrylate are introduced into a 500 ml glass two-necked round-bottomed flask equipped with a condenser and a magnetic stirring device, and maintained under argon. The solution is brought to a temperature of 70° C., and 4.27 g of azobisisobutyronitrile (AIBN) are added to the reaction mixture. The reaction is maintained at this temperature for two hours. A $^1$H NMR analysis confirms that the acrylate monomer has been completely polymerized. The molar mass of the polymer is measured by stearic exclusion chromatography. Mn=1800 g/mol.

2.13 g of azobisisobutyronitrile are added to the polymer derived from the first step, maintained at 70° C. A mixture containing 173.3 g of acrylic acid, 404.7 g of quaternized 2-dimethylaminoethyl acrylate, 335 g of water and 335 g of ethanol is subsequently added for 4 hours. After introduction for 2 hours, 3.2 g of AIBN are introduced. At the end of the 4 hours of introduction of the monomer solution, 3.2 g of AIBN are again introduced into the reactor. The reaction is then maintained at this temperature for a further 2 hours.

A $^1$H NMR analysis confirms that the composition of the final copolymer corresponds to that expected.

The invention claimed is:

1. A controlled structure copolymer comprising a (block A)-(block B) diblock copolymer, a (block A)-(block B)-(block A) triblock copolymer or a (block B)-(block A)-(block B) triblock copolymer
   wherein block A comprises ionic or potentially ionic units, and further wherein:
   block A is amphoteric and comprises:
   cationic or potentially cationic units $A_C$, anionic or potentially anionic units $A_A$, and optionally, hydrophilic and/or hydrophobic neutral units $A_N$,
   block B is not amphoteric or zwitteriornic.

2. The copolymer of claim 1, wherein block B is a hydrophilic or hydrophobic neutral block comprising hydrophilic or hydrophobic neutral units.

3. The copolymer as claimed in claim 1, wherein said copolymer is obtained by a controlled radical polymerization.

4. The copolyrner of claim 1, wherein block B is a neutral block, and block A has a positive, negative or neutral average charge.

5. The copolymer of claim 1, wherein said copolymer is in the form of a powder, a dispersion in a liquid, or a solution.

6. The copolymer of claim 1, wherein the units $A_C$ are derived from monomers comprising:
   N,N-(dialkylamino-m-alkyl)amidcs of α,β-monoethylenically unsaturated carboxylic acids,
   αβ-monoethylenically unsaturated amino esters,
   vinylpyridines,
   vinylamine,
   vinylimidazolines,
   monomers that are precursors of amine functions which give rise to primary amine functions by simple acid or base hydrolysis,
   acryloyl- or acryloyloxyammonium monomers,
   N,N-dialkyldiallylamine monomers,
   polyquaternary monomers, or
   mixtures thereof.

7. The copolymer of claim 6, wherein the units $A_C$ are derived from monomers comprising:
   N,N-dimethylaminomethylacrylamide, N,N-dimethylaminomethymethacrylamide, 2-(N,N-dimethylamino)ethylacrylamide, 2-(N,N-dimethylamino)ethylmethacrylamide, 3-(N,N-dimethylamino)propylacrylamide 3-(N,N-dimethylamino)propyl methacrylamide, 4-(N,N-dimethylamino)butylacrylamide, 4-(N,N-dimethylamino)butylmethacrylamide, 2-(dimethylamino)ethyl acrylate (DMAA), 2-(dimethylamino)ethyl methacrylate (DMAM), 3-(dimethylaniino)propyl methacrylate, 2-(tert-butylamino)ethyl methacrylate, 2-(dipentylamino)ethyl methacrylate, 2(dierhylamino)ethyl methacrylate, N-vinylformamide, N-vinylacetamide,
   trimethylammonium propyl methacrylate chloride, trimethylammonium ethylacrylamide chloride, trimethylammonium ethylacrylamide bromide, trimethylammonium ethylmethacrylamide chloride, trimethylammonium ethylmethacrylamide bromide, trimethylammonium butylacrylamide methyl sulfate, trimethylammonium butylrnethacrylamide methyl sulfate, trimethylammonium propylmethacrylamide methyl sulfate (MES), (3-methacrylamidopropyl)trimethylammonium chloride (MAPTAC), (3-acrylamidopropyl)trimethylammonium chloride (APTAC), methacryloyloxyethyl-trimethylammonium chloride, methacryloyloxyethyltrimethylammonium methyl sulfate, acryloyloxyethyltrimethylammonium chloride, 1-ethyl-2-vinylpyridinium bromide, 1-ethyl-2-vinylpyridinium chloride, 1-ethyl-2-vinylpyridinium methyl sulfate, 1-ethyl-4-vinylpyridinium bromide, 1-ethyl-4-vinylpyridinium chloride, 1-ethyl-4-vinylpyridinium methyl sulfate;

N,N-dimethyldiallylammonium chloride (DADMAC);

dimethylaminopropylmethacrylamide chloride, or N-(3-chloro-2hydroxypropyl)trimethylan-imonium (DIQUAT), trimethylammonium ethyl acrylate methyl sulfate (ADAMquat), or mixtures thereof.

8. The copolymer of claim 1, wherein the units $A_A$ are derived from monomers comprising:
   α,β-ethylenically unsaturated carboxylic acids or corresponding anhydrides, or their water-soluble salts;
   precursors of carboxylate functions, which, after polymerization, form carboxylic functions by hydrolysis;
   monomers having at least one sulfate or sulfonate function, or their water-soluble salts;
   monomers having at least one phosphonate or phosphate function, the esters of ethylenically unsaturated phosphates, or their water-soluble salts; or mixtures thereof.

9. The copolymer of claim 8, wherein the units $A_A$ comprise acrylic, methacrylic or maleic acids or anhydrides, fumaric acid, itaconic acid, N-methacroylailanine, N-acryloylgtycine, tert-butyl acrylate, 2-sulfooxyethyl methacrylate, vinylbenzene sulfonic acid, allyl sulfonic acid, 2-acrylamido-2-methylpropane sulfonic acid, sulfoethyl acrylate or methacrylate, sulfopropyl acrylate or methacrylate, vinylphosphonic acid, the phosphates derived from hydroxyethyl methacrylate or the phosphates derived from polyoxyalkylene methacrylates.

10. The copolymer of claim 1, wherein block B comprises units derived from hydrophobic neutral monomers comprising:
    vinylaromatic monomers,
    vinyl halides, vinylidene halides,
    $C_1$-$C_{12}$ alkylesters of α, β-monoethylenically unsaturated acids vinyl esters of saturated carboxylic acids, allyl esters of saturated carboxylic acids, α, β-monoethylenically unsaturated nitriles having from 3 to 12 carbon atoms,
    α-olefins,
    conjugated dienes,
    monomers capable of generating polydimethylsiloxane chains, or
    mixtures thereof.

11. The copolymer of claim 10, wherein the units of block B are derived from hydrophobic neutral monomers comprising:
    styrene, aipha-methyistyrene, vinyitoluene,
    vinyl chloride, vinylidene chloride,
    methyl, ethyl or butyl acrylates and methacrylates, 2-ethylhexyl acrylate,
    vinyl or allyl acetates, propionates, versatates, stearates, acrylonitrile, methacrylonitrile,
    ethylene,
    butadiene, isoprene, chioroprene, or
    mixtures thereof.

12. A detergent composition, fabric care composition, or composition for cleansing, treating and/or protecting the skin and/or the hair, comprising the copolymer of claim 1.

13. The copolymer of claim 1, wherein block A is a random block.

14. The copolymer of claim 1, wherein block A comprises a composition gradient.

* * * * *